(12) United States Patent
Kozak et al.

(10) Patent No.: US 7,691,062 B2
(45) Date of Patent: Apr. 6, 2010

(54) METHOD AND APPARATUS FOR THE NON-INVASIVE DETERMINATION OF PROMINENT STRUCTURES OF THE BODY OF A HUMAN BEING OR AN ANIMAL

(75) Inventors: Josef Kozak, Tuttlingen (DE); Peter Keppler, Ulm (DE)

(73) Assignees: Aesculap AG, Tuttlingen (DE); Universitaet Ulm, Ulm (DE)

( * ) Notice: Subject to any disclaimer, the term of this patent is extended or adjusted under 35 U.S.C. 154(b) by 657 days.

(21) Appl. No.: 11/586,483

(22) Filed: Oct. 24, 2006

(65) Prior Publication Data

US 2007/0270696 A1 Nov. 22, 2007

Related U.S. Application Data

(63) Continuation of application No. PCT/EP2005/003847, filed on Apr. 12, 2005.

(30) Foreign Application Priority Data

May 25, 2004 (DE) ........................ 10 2004 026 525

(51) Int. Cl.
*A61B 8/00* (2006.01)

(52) U.S. Cl. ...................................... 600/443; 600/437
(58) Field of Classification Search .................. 600/443
See application file for complete search history.

(56) References Cited

U.S. PATENT DOCUMENTS 5,394,875 A 3/1995 Lewis et al.

(Continued)

FOREIGN PATENT DOCUMENTS

DE 697 21 045 4/2003

(Continued)

OTHER PUBLICATIONS

Keppler, P. et al., "Die sonographische Bestimmung der Beingeometrie," *Der Orthopäde*, Dec. 1999, XP-002331181, pp. 1015-1022.

(Continued)

*Primary Examiner*—Long V Le
*Assistant Examiner*—Saurel J Selkin
(74) *Attorney, Agent, or Firm*—Lipsitz & McAllister, LLC (57) ABSTRACT

In a method for the non-invasive determination of the position and orientation of prominent structures inside the body of a human being or an animal, wherein the body is irradiated with ultrasonic radiation in the area of the prominent structure by means of an ultrasonic head which emits ultrasound and receives ultrasound, the ultrasonic radiation reflected on the prominent structure is received, and an image corresponding to the travel time of the reflected radiation is represented on a display, in order to determine the position of the prominent structure in the body, it is proposed that the position and orientation of the ultrasonic head and of the body in the area of the prominent structure be determined by means of a navigation system with the assistance of marking elements fixed to the ultrasonic head and to the body, that a prominent structure be selected on the display, that the position and orientation of the prominent structure relative to the ultrasonic head be determined on the basis of the radiating direction of the ultrasonic head and the measured travel time of the ultrasonic radiation, and that the position and orientation of the prominent structure relative to the body be determined from the position and orientation of the ultrasonic head relative to the body.

5 Claims, 6 Drawing Sheets

U.S. PATENT DOCUMENTS

| | | | |
|---|---|---|---|
| 5,619,999 | A | 4/1997 | Von Behren et al. |
| 5,744,898 | A * | 4/1998 | Smith et al. .................. 310/334 |
| 6,059,727 | A | 5/2000 | Fowlkes et al. |
| 7,047,657 | B2 | 5/2006 | Goeggelmann et al. |
| 2002/0103432 | A1 | 8/2002 | Kawchuk |
| 2002/0147455 | A1* | 10/2002 | Carson ....................... 606/130 |

FOREIGN PATENT DOCUMENTS

| | | |
|---|---|---|
| DE | 102 41 069 | 3/2004 |
| EP | 0 978 822 | 2/2000 |
| EP | 1 484 019 | 12/2004 |
| WO | 00/63719 | 10/2000 |
| WO | 01/06924 | 2/2001 |
| WO | 03/057001 | 7/2003 |
| WO | 2004/001569 | 12/2003 |

OTHER PUBLICATIONS

Strecker, W. et al., "Computertomographische Torsionswinkelbestimmung der unteren Extremitäten," *Unfallchirurg*, 1994, XP-008048047, pp. 609-613.

* cited by examiner

METHOD AND APPARATUS FOR THE NON-INVASIVE DETERMINATION OF PROMINENT STRUCTURES OF THE BODY OF A HUMAN BEING OR AN ANIMAL

This application is a continuation of international application number PCT/EP2005/003847 filed on Apr. 12, 2005.

The present disclosure relates to the subject matter disclosed in international application number PCT/EP2005/003847 of Apr. 12, 2005 and German application number 10 2004 026 525.9 of May 25, 2004, which are incorporated herein by reference in their entirety and for all purposes.

BACKGROUND OF THE INVENTION

The invention relates to a method for the non-invasive determination of the position and orientation of prominent structures inside the body of a human being or an animal, wherein the body is irradiated with ultrasonic radiation in the area of the prominent structure by means of an ultrasonic head which emits ultrasound and receives ultrasound, the ultrasonic radiation reflected on the prominent structure is received, and an image corresponding to the travel time of the reflected radiation is represented on a display.

The invention further relates to an apparatus for performing this method.

To determine certain prominent structures inside a body, for example, certain bone structures, and to locate their exact position and orientation relative to the body, it has so far been necessary to open the body and to detect these structures inside the body with a probe whose position and orientation relative to the body can be determined by means of, for example, a navigation system.

Information on the position and, if required, orientation of the prominent structures relative to the body is thereby obtained.

A drawback of this method is that an opening in the body is required therefor. When such structures are palpated through soft tissue, inaccuracies may occur.

On the other hand, it is known to scan body structures inside the body via ultrasonic radiation. In known ultrasonic scanning methods, ultrasonic radiation is directed into the body via an ultrasonic head, is reflected there at prominent structures, and the reflected radiation is picked up again by the ultrasonic head. The distance of the reflection surfaces from the ultrasonic head can be determined from the travel time, and also the position of the prominent structures from the radiating direction of the ultrasonic head. All in all, the shape of the prominent structures can thereby be detected and imaged, but exact details of position and orientation relative to the body are not obtained.

The object of the invention is to so develop a method of the generic kind that the precise position and orientation of prominent structures in the body can be determined relative to the body without intervening in the body.

SUMMARY OF THE INVENTION

This object is accomplished with a method of the kind described at the outset, in accordance with the invention, in that the position and orientation of the ultrasonic head and of the body in the area of the prominent structure are determined by means of a navigation system with the assistance of marking elements fixed to the ultrasonic head and to the body, a prominent structure is selected on the display, the position and orientation of the prominent structure relative to the ultrasonic head are determined on the basis of the radiating direction of the ultrasonic head and the measured travel time of the ultrasonic radiation, and the position and orientation of the prominent structure relative to the body are determined from the position and orientation of the ultrasonic head relative to the body.

Accordingly, a navigated ultrasonic head is used, and, in addition, the body is navigated. The ultrasonic head makes it possible for a statement to be made about the direction of the ultrasonic radiation and about the distance of the reflecting surface from the ultrasonic head, and this direction of the ultrasonic radiation is related to the position and orientation of the ultrasonic head, which are determined by the navigation system. In this way, all the necessary data are obtained for determining the position and orientation of the reflecting surface and hence of the prominent structure in the body relative to the body. An opening of the body, as is the case when navigated probes are used, is no longer necessary, with the ultrasonic head assuming the role of a "virtual probe".

It is advantageous for an ultrasonic head to be used, which emits and receives ultrasonic radiation via a multiplicity of transmitting and receiving devices, which are arranged in a row and radiate the ultrasonic radiation into a common plane. An entire plane is thereby simultaneously scanned with ultrasonic radiation, and when placing the ultrasonic head on the body, the operator can align the ultrasonic head in such a way that the prominent structure to be detected is optimally imaged on the display, i. e., is clearly visible. This automatically also results in the ultrasonic head being applied in practically always the same way relative to a certain structure, for example, always such that the ultrasonic head runs parallel to an iliac crest. This ensures a largely reproducible scanning of the prominent structure with the ultrasonic radiation.

To enable the image represented on the display to be evaluated, the operator can select certain characteristic points on the image, for example, by moving to an optical mark and storing the corresponding position data of this mark. In some cases, this is, however, not readily possible, as the depicted structures do not enable selection of a certain exact point. It is then advantageous for the prominent structure on the display to be brought into as close congruence as possible with a predefined geometrical structure and for structural data relating to the prominent structure of the body to be determined from the position of the predefined geometrical structure on the display. Such a predefined geometrical structure may be, for example, a straight or a curved line, in particular, it may be, for example, a circle, which is matched with an approximately circular structure of the display so as to obtain as good congruence as possible, where appropriate, only in a certain portion of the predefined geometrical structure.

When a circle is used, it may be advantageous for a sphere to be determined as structural data of the predefined geometrical structure with the circle of the predefined structure as great circle. This sphere is used to characterize a certain prominent structure.

The method described may be performed at various locations on the body. In a particularly preferred embodiment, provision is made for the left and right iliac crests and, in addition, the symphysis of the hip bone to be selected as prominent structure.

Herein it is advantageous for one prominent point to be determined from each of the two iliac crest images and from the symphysis image on the display and for a plane which is characteristic of the hip bone to be calculated from these three points.

In particular, the characteristic plane may be selected such that a characteristic point of the symphysis, which is directly determinable from the display, lies in it, and that spheres whose surface is contacted by the characteristic plane are associated in the above-described manner with the two iliac crests. Such a plane may be referred to as characteristic plane of the hip bone. This plane may, for example, serve as basis for the geometrical description of the hip bone and the selection of a hip bone-fixed coordinate system.

The object of the invention is also to propose an apparatus for performing this method.

This object is accomplished with an apparatus for the non-invasive determination of the position and orientation of prominent structures inside the body of a human being or an animal, in accordance with the invention, in that it comprises an ultrasonic head for emitting and receiving ultrasonic radiation and a display device for representing an image corresponding to the travel time of emitted ultrasonic radiation reflected at a prominent structure of the body, in that marking elements which are part of a navigation system are provided for the ultrasonic head and the body, and in that a data processor is provided for determining from the relative position and the relative orientation of the ultrasonic head in relation to the body and from the radiating direction of the ultrasonic head and from the measured travel time of the ultrasonic radiation the position and orientation of a prominent structure represented on the display device relative to the body.

Herein it is advantageous for the ultrasonic head to emit and receive the ultrasonic radiation via a multiplicity of transmitting and receiving devices, which are arranged in a row and radiate the ultrasonic radiation into a common plane. The following description of preferred embodiments of the invention serves to explain the invention in greater detail in conjunction with the drawings.

DETAILED DESCRIPTION OF THE INVENTION

Figure 1:
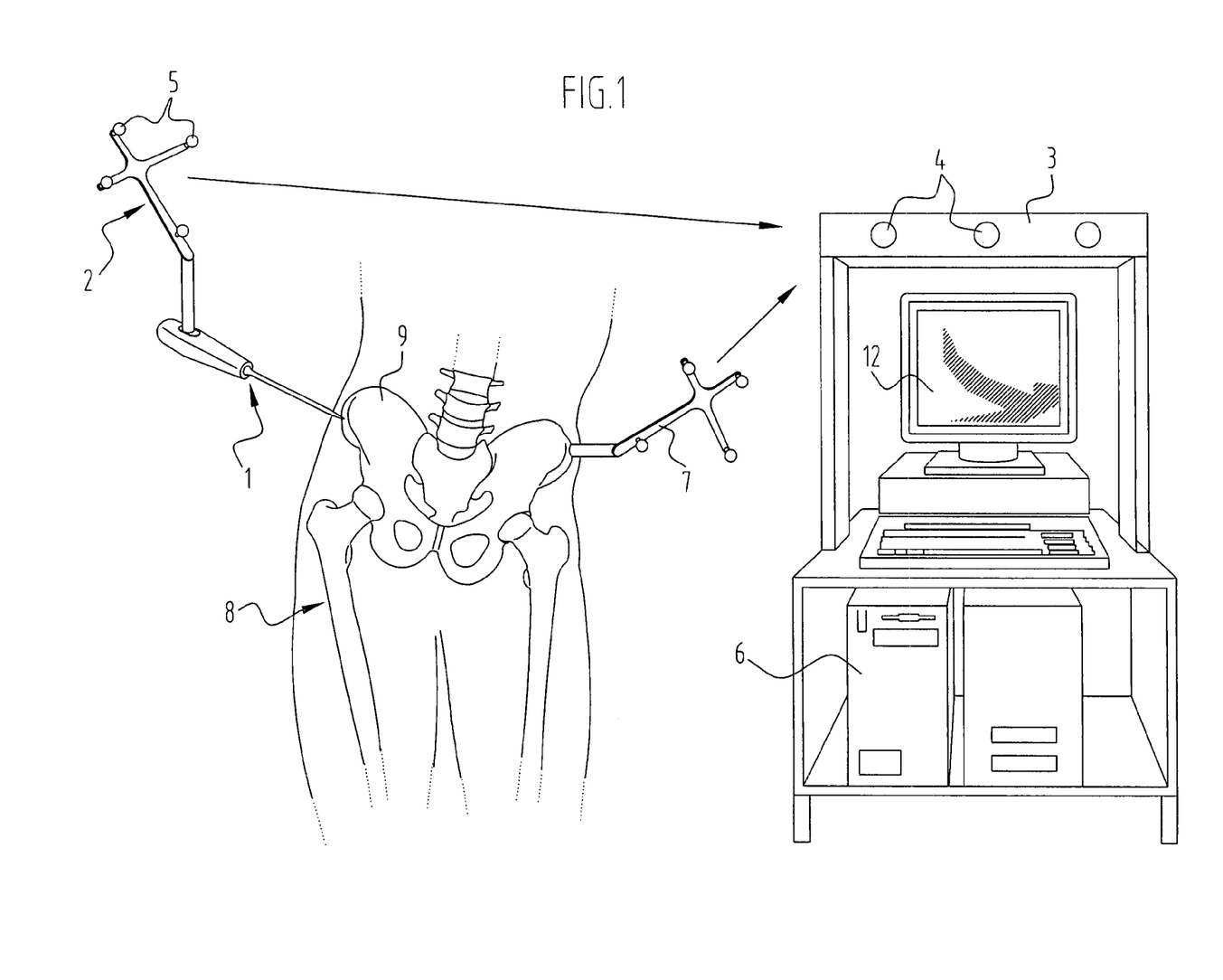
FIG. 1 shows a diagrammatic view of a navigated mechanical probe for palpating prominent structures in the body in accordance with the state of the art.

FIG. 1 shows a conventional apparatus for mechanically palpating a prominent structure of the body. This apparatus comprises a mechanical probe 1, to which a marking element 2 of a conventional navigation system 3 is fixed. This navigation system 3 comprises several transmitting and receiving units 4, which emit electromagnetic radiation, which is reflected at reflectors 5 of the marking element 2 and is picked up again by the transmitting and receiving units 4. From these signals the navigation system 3 can determine in a manner known per se the exact position and orientation of the marking element 2 and hence of the probe 1 in space. The corresponding position data are fed to a data processor 6.

A further marking element 7 which is of the same design as the marking element 2, is attached to a part of the body 8, whose prominent structure is to be determined. In the illustrated embodiment, the marking element 7 is fixed to a hip bone 9, for example, by means of a bone screw which is screwed into the hip bone 9. Such marking elements are normally used for operations and then serve to determine the position and orientation of the corresponding body part during the operation.

It is, however, also readily possible to arrange such marking elements on the unopened body, for example, with the assistance of holders which are fixed to the outside of the body through the soft tissue parts. Bands, etc. may be used for such fixing.

In this way, the navigation system 3 can determine both position and orientation of the probe 1 and position and orientation of the body part on which a structure is to be localized. This localization is carried out with the apparatus illustrated in FIG. 1, which corresponds to the known state of the art, by the tip of the probe 1 being placed on the corresponding structure, for which purpose, the body must be open and the corresponding structure must be freely exposed.

In order to circumvent this, instead of a mechanical probe, an ultrasonic head 10, which is known per se for examining structures inside the body and is designed for placement with a bearing surface 11 against the outside of the body, is used in a method, as explained hereinbelow with reference to FIGS. 2 to 7. Such an ultrasonic head 10 emits, for example, via a plurality of transmitting and receiving units arranged in a row, ultrasonic radiation into a plane common to all transmitting and receiving units and receives ultrasonic radiation that is cast back in this plane and reflected at internal body structures. The distance of the reflecting surface on the internal structure of the body from the ultrasonic head 10 can be determined from the travel time between emitting and receiving the radiation, and these data are fed to the data processor 6.

The marking element 2 is attached to the ultrasonic head 10, so that the position of the ultrasonic head and its orientation can be determined by the navigation system 3.

The pattern generated by the ultrasonic head 10 is represented on a display screen 12, so that the operator can read the relief pattern of the ultrasonic radiation, i. e., the travel time measurements of the ultrasonic radiation, on the display screen 12. This pattern shows certain structures which result from the structure of the surface reflecting the ultrasonic radiation, for example, a bone surface.

Figure 2:
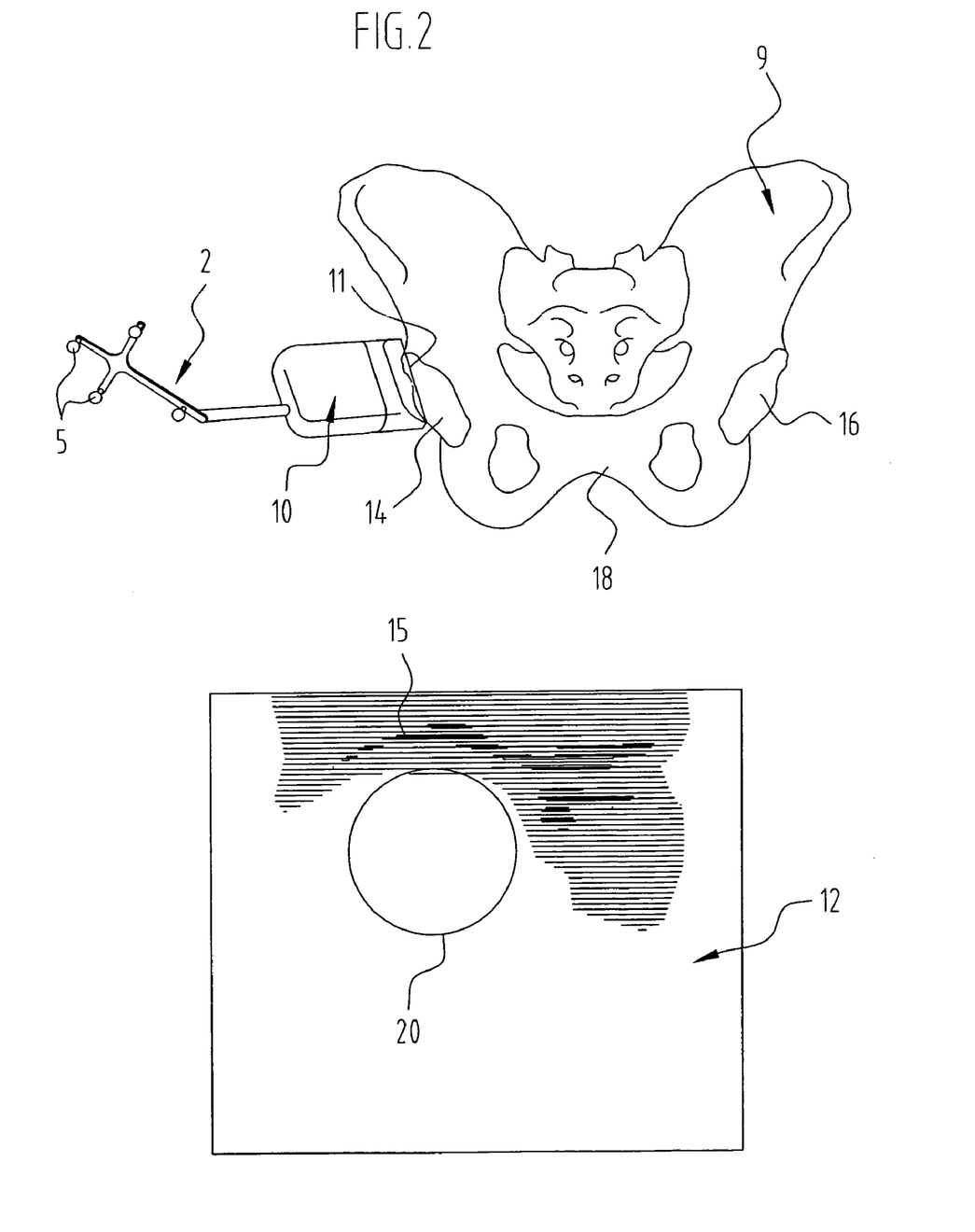
FIG. 2 shows a diagrammatic view of a navigated ultrasonic head placed against an iliac crest of the hip bone with an associated representation of the image generated by the ultrasonic head on a display device.
Figure 3:
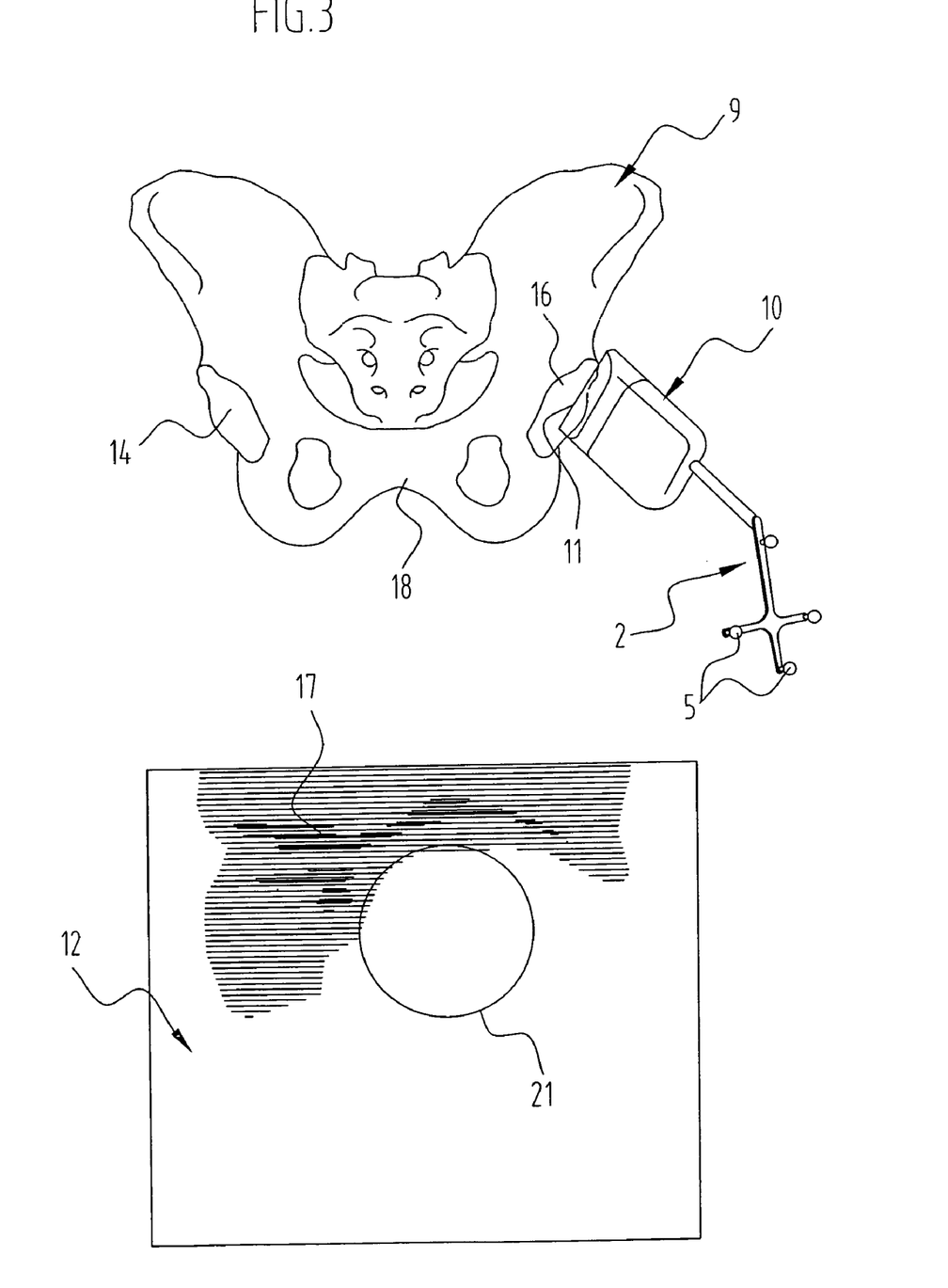
FIG. 3 shows a view similar to FIG. 2 with the ultrasonic head placed against the other iliac crest.
Figure 4:
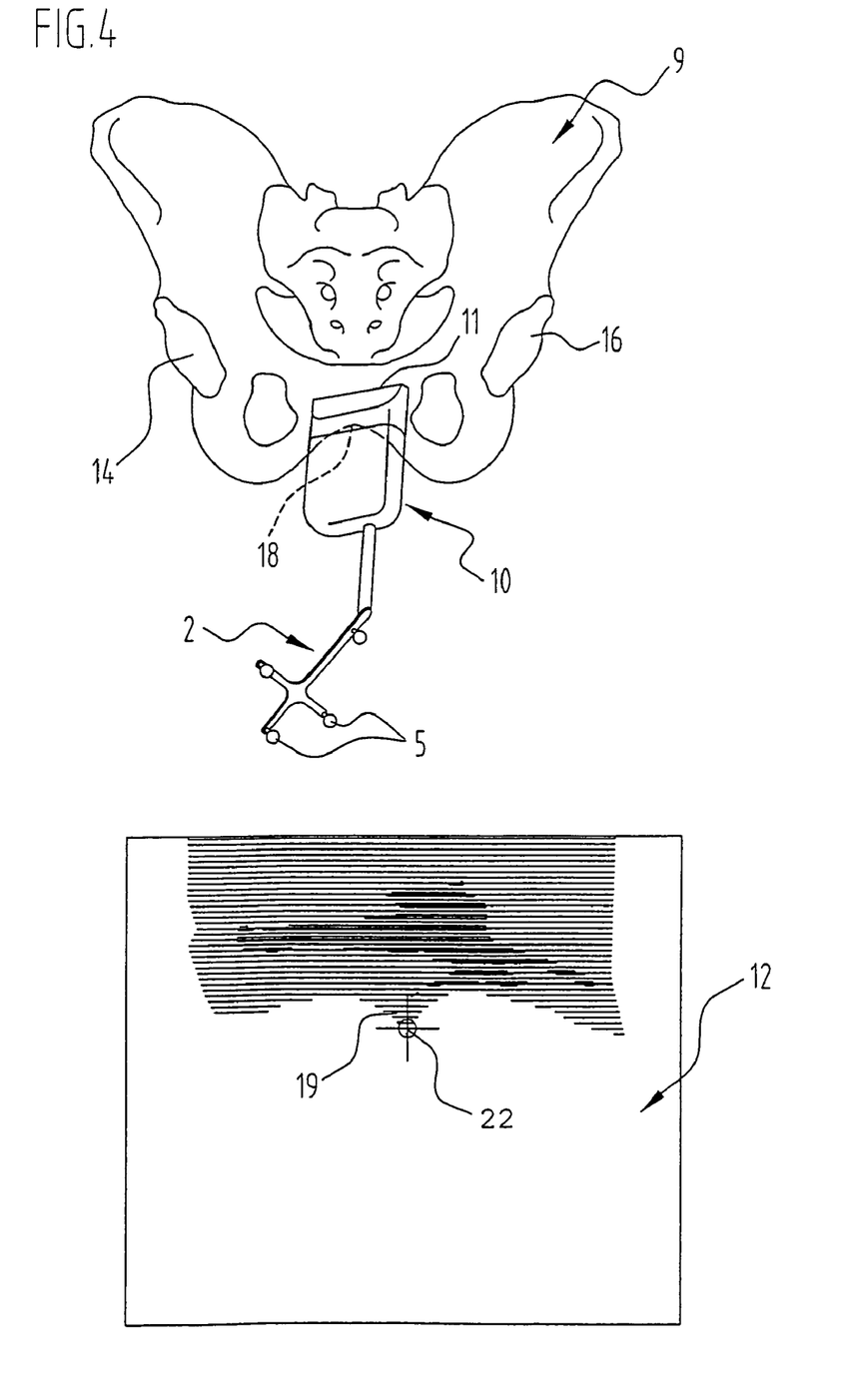
FIG. 4 shows a view similar to FIG. 2 with the ultrasonic head placed against the symphysis of the hip bone.

With a hip bone 9, by way of example, it will be explained with reference to FIGS. 2 to 4 how in this way certain structures of the hip bone can be determined and how these structures can be used to characterize the hip bone.

The ultrasonic head 10 is first placed at a side of the hip bone 9 on the body 8 in such a way that it is substantially in alignment with the iliac crest 14. The precise alignment can be carried out by the operator on the basis of the display on the display screen 12, as a particularly distinct and clearly recognizable structure results from exact alignment with the iliac crest 14, and, as a result, the ultrasonic head can be placed in a largely reproducible manner on hip bones 9 of different patients.

An image which is characteristic of this iliac crest 14 of the hip bone 9 is thereby obtained on the display screen 12. Arcuate areas 15 are clearly recognizable in this image.

This procedure is carried out in the same way at the opposite iliac crest 16. A substantially identical representation with arcuate areas 17 is thereby obtained on the display screen 12.

In a third step, the ultrasonic head is placed at the center of the hip bone 9 at the lower end thereof in the area of the symphysis 18. A tip 19 pointing clearly downwards and reflecting the structure of the symphysis is thereby obtained on the display screen 12.

To obtain the necessary position and orientation data from the imaged structures, symbols with a predefined geometrical structure, for example, circles 20, 21 (FIGS. 2 and 3) and points 22 (FIG. 4) may be depicted and shifted on the display screen 12. The operator can shift these symbols on the display screen 12 in such a way that a deliberate coordination with the ultrasonic images shown is obtained. For example, the circles 20 and 21 can be placed optimally on the arcuate areas 15 and 17, respectively, and the point 22 can be placed on the tip 19. In this way, sets of geometrical data can be determined, which are fed to the data processor 6 and are respectively characteristic of the body areas and prominent structures that are irradiated with the ultrasonic head.

Figure 5:
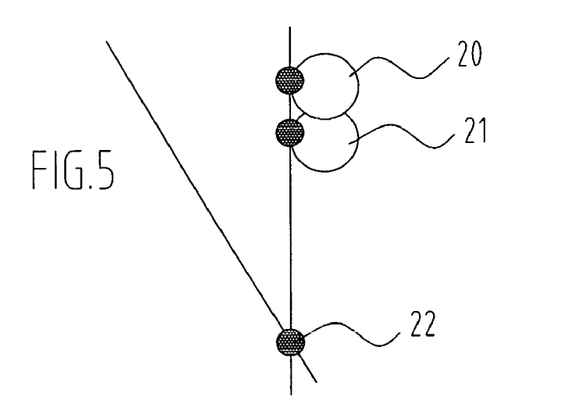
FIG. 5 shows a diagrammatic representation for evaluation of the images of FIGS. 2 to 4 and for determination of a plane which is characteristic of the hip bone.
Figure 6:
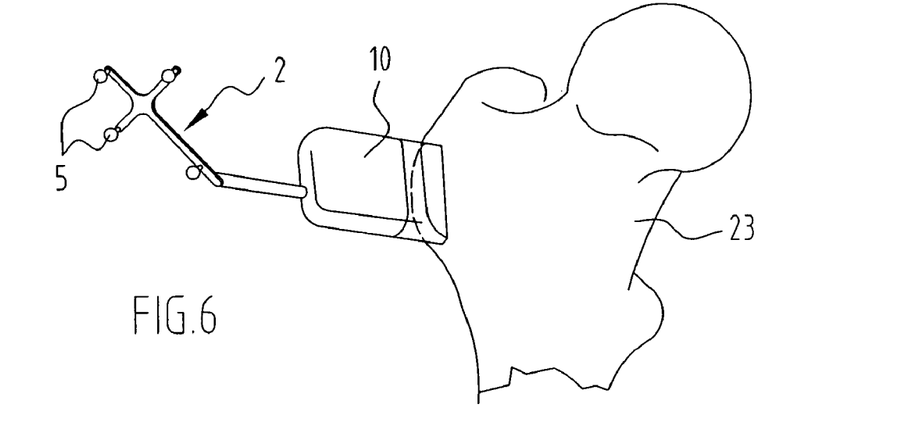
FIG. 6 shows a view similar to FIG. 2 with the ultrasonic head placed against a femur.

The data processor places through the two circles 20, 21 a sphere which has the same center point and the same radius as the circles, so that the circles form great circles. The data processor then calculates from the position of the point 22, on the one hand, and the spheres determined in this way, on the other hand, a plane in which the point 22 is located and which lies tangentially on the two spheres (FIG. 5). A point of each iliac crest 14 lies in this plane, as the circles 20, 21 were placed against the arcuate areas 15, 17 of the iliac crest, so that this also applies to the spheres. A plane is thus determined, which contains one point of each iliac crest and the point determined at the symphysis. Such a plane is a plane that is characteristic of the position and orientation of the hip bone, and this plane can be used to determine at a further stage of the operation a hip bone's own coordinate system and to carry out necessary positionings of implants, machining tools, etc. relative to the hip bone.

Figure 7:
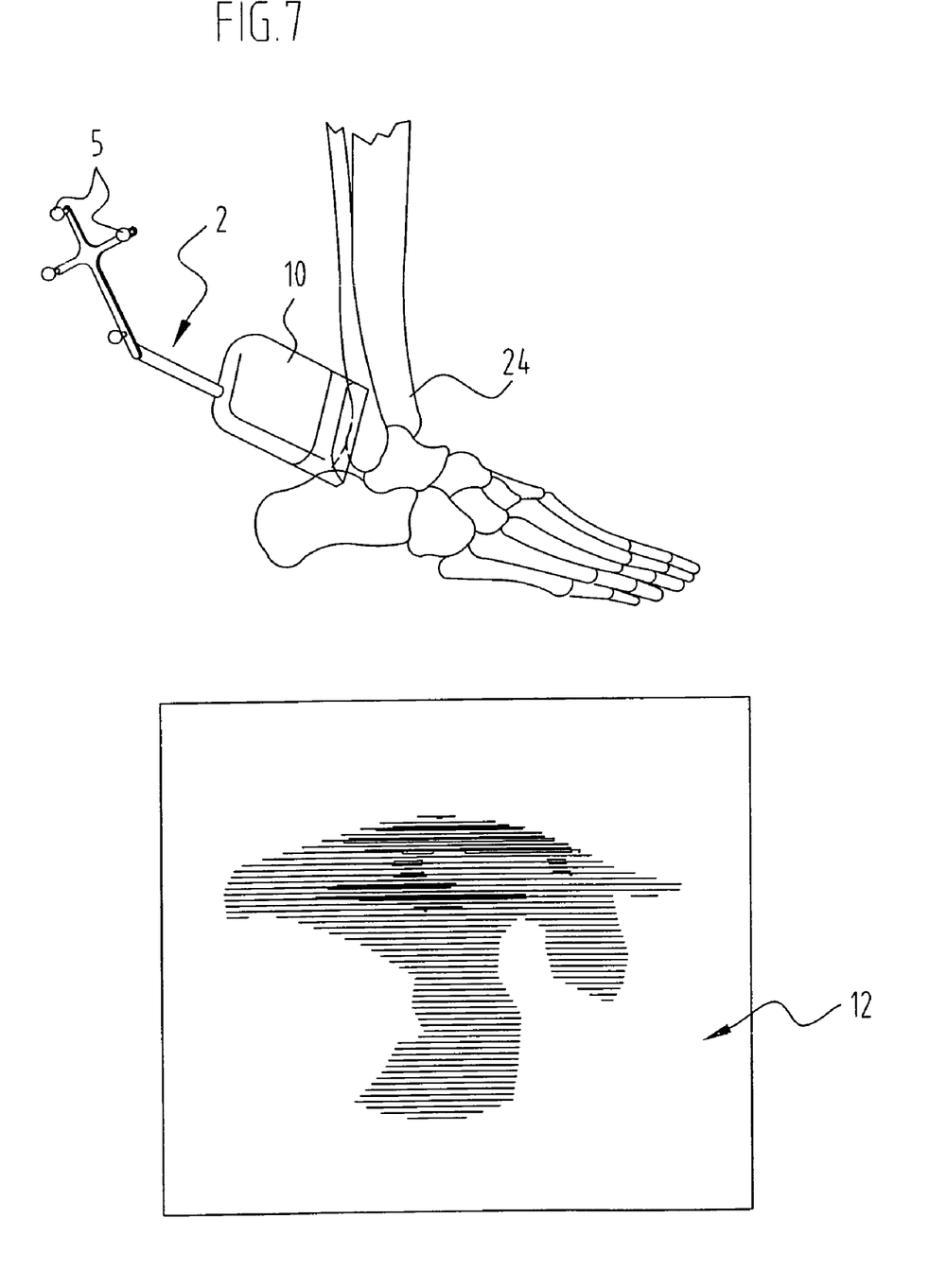
FIG. 7 shows a view similar to FIG. 2 with the ultrasonic head placed against an ankle joint.

The contactless determination of characteristic body structures is explained hereinabove with reference to the hip bone, by way of example. Prominent structures can be located in a similar manner on other body parts, for example, at the end of a femur 23 on the hip joint side thereof (FIG. 6), to which the ultrasonic head 10 is applied in a characteristic manner, or at the end of a tibia 24 on the ankle side thereof (FIG. 7). These illustrations are merely to be seen as examples of usage. It goes without saying that the ultrasonic head 10 is applied to the outside of the body. It is, therefore, not necessary to open the body in order to palpate the structures inside the body.

The invention claimed is:

1. Method for non-invasive determination of a position and orientation of prominent structures inside a body of a human being or an animal, comprising:
   irradiating the body with ultrasonic radiation in an area of the prominent structures by means of an ultrasonic head which emits ultrasound and receives ultrasound,
   receiving the ultrasonic radiation reflected from the prominent structures,
   representing an image corresponding to a travel time of the reflected radiation on a display,
   determining the position and orientation of the ultrasonic head and of the body in the area of the prominent structures by means of a navigation system and marking elements fixed to the ultrasonic head and to the body,
   selecting iliac crests of a hip bone as prominent structures on the display, the position and orientation of the selected prominent structures relative to the ultrasonic head being determined based on a radiating direction of the ultrasonic head and a measured travel time of the ultrasonic radiation, and the position and orientation of the prominent structures relative to the body being determined from the position and orientation of the ultrasonic head relative to the body,
   bringing each of the iliac crests into at least approximate congruence with at least a portion of a corresponding circle on the display,
   determining respective spheres as structural data of each of the iliac crests with the corresponding circle comprising a great circle of the respective sphere, and
   selecting a characteristic plane of a hip bone such that a characteristic point of a symphysis of the hip bone lies in the characteristic plane and that the characteristic plane contacts a surface of the two spheres associated with the iliac crests.

2. Method in accordance with claim 1, wherein the ultrasonic head emits and receives the ultrasonic radiation via a multiplicity of transmitting and receiving devices, which are arranged in a row and radiate the ultrasonic radiation into a common plane.

3. Apparatus for non-invasive determination of a position and orientation of a prominent structures inside a body of a human being or an animal, comprising:
   an ultrasonic head for emitting and receiving ultrasonic radiation,
   a display device for representing an image corresponding to a travel time of emitted ultrasonic radiation reflected from prominent structures of the body,
   marking elements which are part of a navigation system provided for the ultrasonic head and the body, and
   a data processor programmed to determine from a relative position and a relative orientation of the ultrasonic head in relation to the body and from a radiating direction of the ultrasonic head and a measured travel time of the ultrasonic radiation the position and orientation of the prominent structures represented on the display device relative to the body; wherein:
   iliac crests of a hip bone are selected as the prominent structures on the display,
   bringing each of the iliac crests into at least approximate congruence with at least a portion of a corresponding circle on the display,
   determining respective spheres as structural data of each of the iliac crests with the corresponding circle comprising a great circle of the respective sphere, and
   selecting on the display a characteristic plane of a hip bone such that a characteristic point of a symphysis of the hip bone lies in the characteristic plane and that the characteristic plane contacts a surface of the two spheres associated with the iliac crests.

4. Apparatus in accordance with claim 3, wherein the data processor is programmed to determine the characteristic plane of the hip bone.

5. Apparatus in accordance with claim 4, wherein the ultrasonic head emits and receives the ultrasonic radiation via a multiplicity of transmitting and receiving devices, which are arranged in a row and radiate the ultrasonic radiation into a common plane.

* * * * *